(12) United States Patent
Anderson et al.

(10) Patent No.: US 11,605,179 B2
(45) Date of Patent: Mar. 14, 2023

(54) SYSTEM FOR DETERMINING ANATOMICAL FEATURE ORIENTATION

(71) Applicant: Intel Corporation, Santa Clara, CA (US)

(72) Inventors: Glen J. Anderson, Beaverton, OR (US); Giuseppe Raffa, Portland, OR (US); Carl S. Marshall, Portland, OR (US); Meng Shi, Hillsboro, OR (US)

(73) Assignee: Intel Corporation, Santa Clara, CA (US)

( * ) Notice: Subject to any disclaimer, the term of this patent is extended or adjusted under 35 U.S.C. 154(b) by 0 days.

(21) Appl. No.: 17/840,077

(22) Filed: Jun. 14, 2022

(65) Prior Publication Data

US 2022/0392100 A1  Dec. 8, 2022

Related U.S. Application Data

(63) Continuation of application No. 16/747,452, filed on Jan. 20, 2020, now Pat. No. 11,410,326, which is a
(Continued)

(51) Int. Cl.
*G06K 9/00* (2022.01)
*G06T 7/70* (2017.01)
(Continued)

(52) U.S. Cl.
CPC ............. *G06T 7/70* (2017.01); *A61B 90/361* (2016.02); *G06F 3/012* (2013.01); *G06K 9/6271* (2013.01);
(Continued)

(58) Field of Classification Search
None
See application file for complete search history.

(56) References Cited

U.S. PATENT DOCUMENTS 6,714,665 B1 * 3/2004 Hanna .................... G06V 40/19
382/209
8,452,051 B1 * 5/2013 Lee ......................... G06F 3/011
382/103

(Continued)

OTHER PUBLICATIONS

Cao, Zhe, et al. "Realtime multi-person 2d pose estimation using part affinity fields." Proceedings of the IEEE conference on computer vision and pattern recognition. 2017. (Year: 2017).*

(Continued)

*Primary Examiner* — Avinash Yentrapati
(74) *Attorney, Agent, or Firm* — Hanley, Flight & Zimmerman, LLC

(57) ABSTRACT

The systems and methods disclosed herein provide determination of an orientation of a feature towards a reference target. As a non-limiting example, a system consistent with the present disclosure may include a processor, a memory, and a single camera affixed to the ceiling of a room occupied by a person. The system may analyze images from the camera to identify any objects in the room and their locations. Once the system has identified an object and its location, the system may prompt the person to look directly at the object. The camera may then record an image of the user looking at the object. The processor may analyze the image to determine the location of the user's head and, combined with the known location of the object and the known location of the camera, determine the direction that the user is facing. This direction may be treated as a reference value, or "ground truth." The captured image may be associated with the direction, and the combination may be used as training input into an application.

20 Claims, 5 Drawing Sheets

Related U.S. Application Data continuation of application No. 15/639,555, filed on Jun. 30, 2017, now Pat. No. 10,540,778.

(51) Int. Cl.
| | |
|---|---|
| *A61B 90/00* | (2016.01) |
| *G06F 3/01* | (2006.01) |
| *G06K 9/62* | (2022.01) |
| *G06V 10/44* | (2022.01) |
| *G06V 30/194* | (2022.01) |
| *G06V 40/16* | (2022.01) |
| *A61B 5/00* | (2006.01) |

(52) U.S. Cl.
CPC .......... *G06V 10/454* (2022.01); *G06V 30/194* (2022.01); *G06V 40/168* (2022.01); *A61B 5/70* (2013.01); *G06T 2207/30196* (2013.01)

(56) References Cited

U.S. PATENT DOCUMENTS

| | | | |
|---|---|---|---|
| 10,540,778 B2 | 1/2020 | Anderson et al. | |
| 10,705,598 B2 * | 7/2020 | Steedly | A63F 13/80 |
| 11,010,972 B2 * | 5/2021 | Wiley | G06F 3/017 |
| 11,410,326 B2 | 8/2022 | Anderson et al. | |
| 2009/0141941 A1 * | 6/2009 | Wagg | G06T 7/75 |
| | | | 382/103 |
| 2010/0215271 A1 * | 8/2010 | Dariush | G06V 40/103 |
| | | | 382/180 |
| 2010/0303303 A1 * | 12/2010 | Shen | G06V 40/20 |
| | | | 382/107 |
| 2011/0128223 A1 * | 6/2011 | Lashina | G06F 3/012 |
| | | | 345/158 |
| 2013/0083976 A1 * | 4/2013 | Ragland | G06V 40/168 |
| | | | 382/117 |
| 2016/0080732 A1 * | 3/2016 | Pedley | H04N 13/344 |
| | | | 345/8 |
| 2016/0227190 A1 * | 8/2016 | Cole | H04N 13/161 |
| 2017/0011555 A1 * | 1/2017 | Li | G02B 27/0101 |
| 2017/0154441 A1 * | 6/2017 | Kawaguchi | G06T 7/73 |
| 2017/0208416 A1 * | 7/2017 | Petrov | G02B 27/0093 |
| 2017/0228888 A1 * | 8/2017 | Kawaguchi | G06T 7/90 |
| 2017/0330387 A1 * | 11/2017 | Dearman | G02B 27/017 |
| 2018/0005395 A1 * | 1/2018 | D'Angelo | G08B 21/0461 |
| 2018/0012413 A1 * | 1/2018 | Jones | G06T 19/006 |
| 2018/0020978 A1 * | 1/2018 | Kaifosh | G06F 3/011 |
| | | | 702/150 |
| 2018/0075659 A1 * | 3/2018 | Browy | G02B 27/017 |
| 2018/0091732 A1 * | 3/2018 | Wilson | G06F 3/048 |
| 2019/0058859 A1 * | 2/2019 | Price | H04N 13/271 |

OTHER PUBLICATIONS

United States Patent and Trademark Office, "Non-Final Office Action", issued in connection with U.S. Appl. No. 15/639,555, filed Mar. 8, 2019, 9 pages.

United States Patent and Trademark Office, "Notice of Allowance and Fee(s) Due", issued in connection with U.S. Appl. No. 15/639,555, filed Sep. 16, 2019, 9 pages.

Insafutdinov, Eldar et al., "ArtTrack: Articulated Multi-person Tracking in the Wild," Max Planck Institute for Informatics Saarland Informatics Campus, Saabreucken, Germany, arXiv:1612.01465v2 [cs.cv] Dec. 22, 2016, 9 pages.

Cao, She, et al.: "Realtime Multi-Person 2D Pose Estimation using Part Affinity Fields", arXiv: 1611.08050v1 [cs.CV], Nov. 24, 2016, http://posefs1.perception.cs.cmu.edu/Users/ZheCao/humanpose.mp4, 9 pages.

Insafutdinov, Eldar, et al.: "DeeperCut: A Deeper, Stronger, and Faster Multi-Person Pose Estimation Model", arXiv: 1605.03170v1 [cs.CV], May 10, 2016, Models and code available at http://pose.mpi-inf.mpg.de, 22 pages.

United States Patent and Trademark Office, "Notice of Allowability," issued in connection with U.S. Appl. No. 16/747,452, filed Jul. 14, 2022, 2 pages.

United States Patent and Trademark Office, "Notice of Allowance and Fee(s) Due," issued in connection with U.S. Appl. No. 16/747,452, filed Mar. 16, 2022, 7 pages.

United States Patent and Trademark Office, "Non-Final Office Action", issued in connection with U.S. Appl. No. 16/747,452, filed Oct. 4, 2021, 6 pages.

* cited by examiner

SYSTEM FOR DETERMINING ANATOMICAL FEATURE ORIENTATION

CROSS-REFERENCE TO RELATED APPLICATIONS

The present application is a continuation of U.S. application Ser. No. 16/747,452, which was filed on Jan. 20, 2020, which is continuation of U.S. application Ser. No. 15/639,555, which was filed on Jun. 30, 2017. Priority if claimed to U.S. application Ser. No. 16/747,452 and U.S. application Ser. No. 15/639,555. U.S. application Ser. No. 16/747,452 and U.S. application Ser. No. 15/639,555 are hereby incorporated by reference in their entireties.

TECHNICAL FIELD

The present disclosure relates to systems and methods for determining anatomical feature orientation.

BACKGROUND

Tracking orientation of a person's head, especially the face, is helpful in many applications. It can inform an application about the direction in which a person is looking or speaking, and it is a helpful in locating facial features to recognize facial expressions or perform face recognition. It can also allow a system to know where a user is probably attending (what they are paying attention to). This is important, for example, for an agent to know whether a user is looking at a projected display, some other object, or another person. At other times, it may be valuable for an agent to be able to determine the source of a voice.

However, sometimes camera and/or microphone coverage of a space is limited, and if the person does not look at a camera directly, exposing the face, systems have difficulty determining which direction a person is looking when relying on face detection/face recognition algorithms. Also, sometimes due to camera position, it may be desirable to track which direction a person is facing without visibility to the face. This could be done with training to a person's head shape, but a reference value ("ground truth") about the orientation of a person's head is difficult to establish without substantial cooperation (training sessions) from people. The same is true about ground truth about which direction a user is facing for voice-source determination.

In modern systems based on machine learning technologies to train a recognition system, usually a significant amount of training data is needed to obtain acceptable performance. Lately, with deep learning approaches, this need has increased even further. For example, considering vision techniques, training under different lighting conditions and occlusions is desirable, hence training data under realistic conditions (vs. lab data or obtained from small training sessions) is needed to obtain state-of-the-art performance. Furthermore, it is recommended to continue to collect training data even when the system is performing recognition, such as when using personalized or adaptive models.

BRIEF DESCRIPTION OF THE DRAWINGS

Features and advantages of various embodiments of the claimed subject matter will become apparent as the following Detailed Description proceeds, and upon reference to the Drawings, wherein like numerals designate like parts, and in which:

Although the following Detailed Description will proceed with reference being made to illustrative embodiments, many alternatives, modifications and variations thereof will be apparent to those skilled in the art.

DETAILED DESCRIPTION

The systems and methods disclosed herein provide determination of an orientation of a feature towards a reference target. As a non-limiting example, a system consistent with the present disclosure may include a processor, a memory, and a single camera affixed to the ceiling of a room occupied by a person. The system may analyze images from the camera to identify any objects in the room and their locations. Once the system has identified an object and its location, the system may prompt the person to look directly at the object. The camera may then record an image of the user looking at the object. The processor may analyze the image to determine the location of the user's head and, combined with the known location of the object and the known location of the camera, determine the direction that the user is facing. This orientation of the user's head may be treated as a reference value, or "ground truth." The captured image may be associated with the direction, and the combination may be used as training input into an application.

The application may also analyze the image (without the known location of the object) and produce its own estimate of the direction that the user is facing. The application may utilize machine learning and be trained based on comparisons of its analysis of an image to the known ground truth direction associated with that image. This training may be repeated a plurality of times (with different objects or images) until the application is sufficiently accurate. Accuracy may be determined based on a single comparison, e.g., the output of the subsystem for an image is within a threshold of the ground truth for the same image, or based upon statistical trends over multiple comparisons.

Throughout this disclosure, reference may be made to an "environment" (such as environment 200 in FIG. 2) or "room." While many embodiments describe components of this disclosure being located in the same room, this is meant as a non-limiting example; in some embodiments, no particular room is necessary. Some or all of the systems, components, or users described herein may be located in separate rooms, buildings, outdoor areas, etc.

Figure 1:
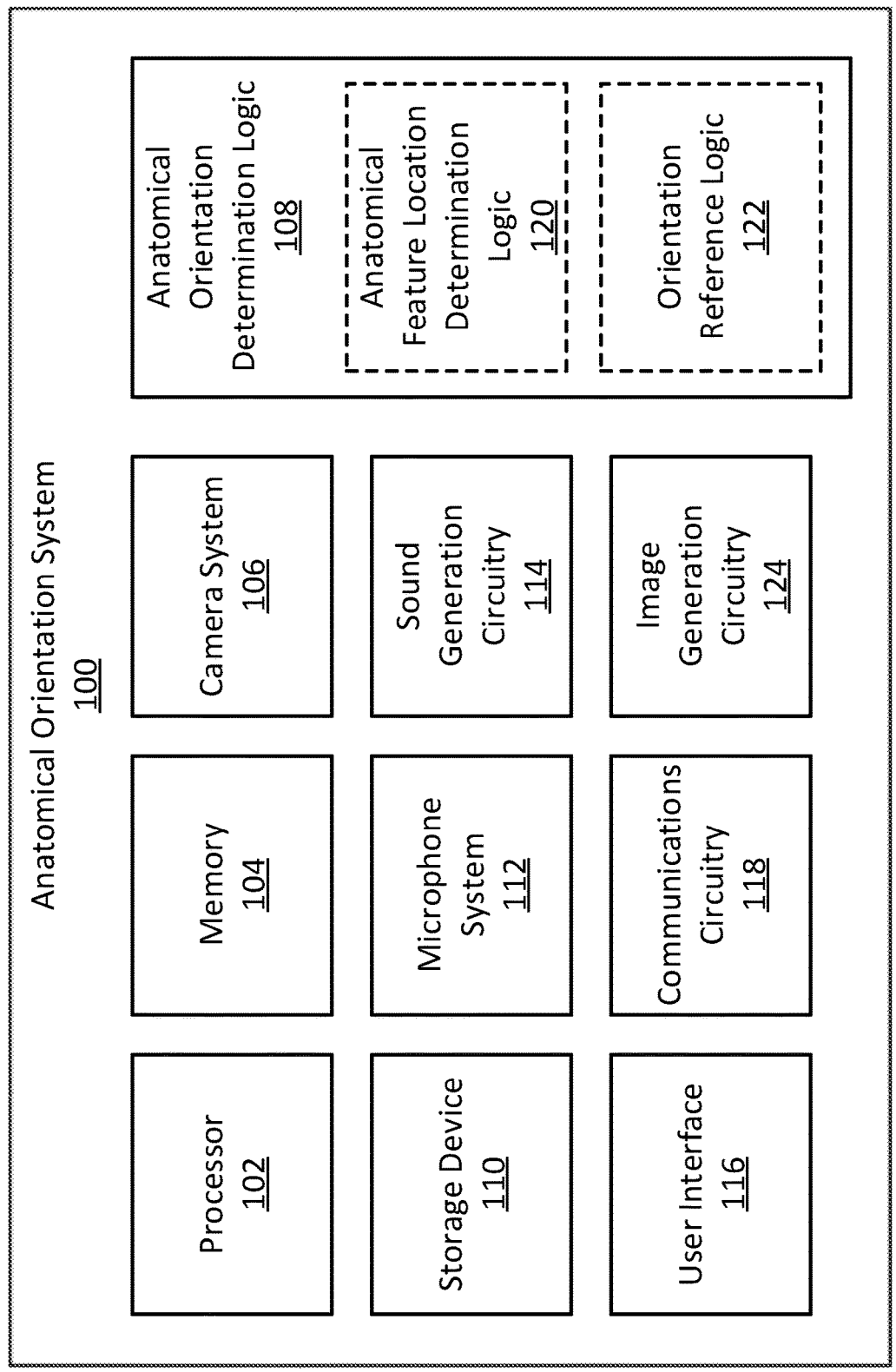
FIG. 1 illustrates an anatomical orientation system according to several embodiments of the present disclosure.

FIG. 1 illustrates an anatomical orientation system 100 consistent with several embodiments of the present disclosure. The system 100 generally includes processor 102, memory 104, and camera system 106 configured to detect images within a given environment. The camera system 106 may include one or more camera devices each configured to detect images, for example, in the visible spectrum, infrared spectrum, etc., and may further include depth-detecting cameras such as Time-of-Flight (ToF) cameras, etc. The system 100 also includes anatomical orientation determination logic 108 generally configured to determine an orientation of anatomical feature of a subject in a given environment. The following detailed description will provide specific examples of determining an orientation of a head of a subject, however, the present disclosure is not limited by any particular anatomical feature. The system 100 may also include storage device 110 to store, for example, metadata as may be generated by 108 (described below). In some embodiments, the system 100 may also include a microphone system 112 generally configured to detect sound within a given environment. The microphone system 112 may include for example, one or more microphones. The system 100 may also include sound generation circuitry 114 generally configured to emit audible sounds and user interface circuitry 116 generally configured to enable a user to interact with system 100. The system 100 may also include communications circuitry 118 generally configured to communicate commands and data with another device (not shown). The system 100 may also include image generation circuitry 124 generally configured to generate or project visible images.

In general, the system 100 is configured to determine the orientation of an anatomical feature (e.g., a head) of a subject. Accordingly, the anatomical orientation determination logic 108 includes anatomical feature location determination logic 120 configured to identify an anatomical feature (e.g., head) of a subject when the subject is within the field of view of the camera system 106, and determine the location of the head within a given environment. To identify the head of a subject, logic 120 may utilize identification techniques such as, for example, skeleton tracking, blob analysis, template matching techniques, Viola-Jones algorithm, etc. Such techniques may include custom, proprietary, known and/or after-developed anatomical feature identification instruction sets that are generally well-defined and operable to receive image data and identify a specific anatomical feature (e.g., a head). To determine the location of the head within a given environment, the logic 120 may similarly utilize skeleton tracking, blob analysis, template matching techniques, Viola-Jones algorithm etc. In some embodiments the location of the head may be made in reference to a defined coordinate system relative to the environment (e.g., 3 space XYZ coordinate system, 2 space XY coordinate system, etc.). In other embodiments, the location of the head may be made with reference to a distance from one or more given points in an environment, e.g., distance from a camera within the environment, etc.

In some embodiments, logic 120 may determine if the anatomical feature of the subject is stationary or in motion. This may be performed using, for example, pixel-reading motion detection, skeleton tracking, facial recognition, etc. In some embodiments, a non-stationary anatomical feature may introduce error into the determinations of location and/or orientation. However, in some embodiments, system 100 may be configured to determine location and/or orientation of the anatomical feature even if it is in motion. In these or other embodiments, logic 120 may be configured to track the location of the anatomical feature over time, storing data corresponding to locations at various points in time in, for example, storage device 110, memory 104, etc.

In some embodiments, anatomical feature location determination logic 120 may use one or more sensors on the anatomical feature to determine its location. For example, logic 120 may communicate with (via, e.g., Bluetooth, WiFi, etc.) a compass and/or accelerometers and/or gyroscopes to measure location of the anatomical feature within the XYZ coordinate system. These sensors may provide information with, for example, 3 degrees of freedom (e.g., 3 1-dimensional accelerometers), 9 degrees of freedom (e.g., 3 gyroscopes, a 3-dimensional compass, and 3 1-dimensional accelerometers), etc.

In some embodiments, anatomical feature location determination logic 120 may use microphone system 112 to record a sound emitted by the anatomical feature of the subject (e.g., a spoken voice). Microphone system 112 may comprise a plurality (e.g., 4, 6, etc.) of microphones (individual microphones not shown in FIG. 1). Locations of the microphones of system 112 may be known to system 100 or logic 120, e.g., may be stored in memory 104 or storage device 110. Logic 120 may perform analysis upon the recorded subject-emitted sound(s) including, for example, beam-forming, Time of Arrival (ToA), etc. to triangulate or otherwise determine a location of the source of the sound(s) emitted by the subject. The location of the source may be assumed to be the location of the anatomical feature (e.g., a subject's voice may be assumed to come from the subject's head). Logic 120 may further utilize a model of the acoustics of the environment to determine the location with increased accuracy. Determining the model is described in further detail below.

Logic 120 may be configured to determine or map acoustic properties (reverberation, echo, frequency response, etc.) of the environment. For example, logic 120 may cause sound generation circuitry 114 to emit a sound waveform (e.g., a sine wave, square wave, noisy signal, etc.) and cause microphone system 112 to receive and record the sound. The recorded waveform may be stored in memory, such as memory 104 or storage device 110. Logic 120 may be configured to determine variations between the emitted sound and the recorded waveform using waveform analysis techniques such as, for example, Fourier Analysis, Time-of-Flight (ToF), Time-of-Arrival (ToA), Angle of Arrival (AoA), etc. In some embodiments, logic 120 may cause microphone system 112 to record background sound (i.e., record when sound generation circuitry 114 is idle) to aid in filtering out noise from the recorded waveform. In the same or other embodiments, system 100 may receive user inputs via user interface 116 or communications circuitry 118 to aid in determining acoustic properties of the area. The user inputs may be directed to, for example, room size/dimensions, locations of significant objects (for example, furniture, etc.), etc. Logic 120 may be configured to store these inputs in memory 104 or storage device 110.

Anatomical orientation determination logic 108 also includes orientation reference logic 122 generally configured to cause a subject to orient their head toward a predetermined target. In one embodiment, logic 122 is configured to identify and locate a target object associated with the subject, for example a cell phone, tablet, etc. To identify and locate a target object associated with a subject, logic 122 may utilize identification and location techniques such as, for example, object recognition, etc. Such techniques may include custom, proprietary, known and/or after-developed object recognition instruction sets that are generally well-defined and operable to receive image data and identify an object and the special location of the object. Conventional object recognition techniques include, for example, appearance-based or feature-based analysis techniques, template matching, deep learning, Viola-Jones algorithm etc. In another embodiment, an object within the environment may be used as a target, and such an object may include, for example a known and/or previously identified object within the environment having a known location within the environment. Logic 122 may also be configured to prompt a subject to look generally towards the target using, for example using audile commands and/or queues, visual commands, prompts, queues, etc. For example, if the target is a cell phone of the subject, logic 122 may cause communications circuitry 118 to communicate commands and/or data to the cell phone to prompt the subject to look at their cell phone. In other embodiments, instead of identifying a target object associated with the subject or a target object within the environment, logic 122 may be configured to generate audible and/or visual prompts to instruct and/or cause the subject to look toward a selected location. For example, a subject may be instructed to look at a projected image, look toward a sound, etc.

Logic 122 is also configured to determine an orientation of an identified anatomical feature (e.g., head) based on the location of the head and the location of the target within an environment. In some embodiments, logic 122 is configured to determine a first vector representing the location of the head relative to a coordinate system and/or a fixed point within the environment. Thus, for example, the first vector may represent an estimate of the location of the head relative to a camera. Logic 122 is also configured to determine a second vector representing the location of the target relative to a coordinate system and/or a fixed point within the environment. Logic 122 is also configured to determine a third vector representing a location and direction that the head of a subject is facing, referred to herein as "head orientation vector." Logic 122 may also cause an image capture of the head while the head is looking toward the target and append the head orientation vector information to the image (for example, MPEG 7 metadata, etc.). The appended image data may be stored on storage device 110 and used, for example as training data for applications that require head orientation information, such as, for example, Convolutional Neural Network (CNNs), decision trees, random forest, boosting algorithms, etc.

Determination of the third vector may include an assumption that the subject is generally looking toward the target, so that the head is facing toward the object. However, this assumption may introduce errors if, for example, the subject is moving their eyes toward the target while their head remains relatively stationary. Accordingly, in some embodiments, logic 122 is also configured to track certain features to determine head movement, for example, by tracking eye movement, tracking nose movement, etc. In such embodiments, logic 122 may cause camera system 106 to capture images of the face and determine eye movement using eye tracking techniques, etc. Such techniques may include custom, proprietary, known and/or after-developed tracking instruction sets that are generally well-defined and operable to receive image data and identify and track anatomical features. Conventional tracking techniques may include, for example, appearance-based or feature-based image analysis techniques, template matching, optical flow algorithms, etc. Tracking a subject's facial features may enable a more accurate determination that the subject is facing toward the target.

In some embodiments, logic 122 may be configured to request and receive verification that the anatomical feature is oriented toward the target. For example, if the target is a cell phone of the subject, logic 122 may communicate additional commands and/or data to the cell phone to cause the cell phone to transmit verification. Verification may be received via communications circuitry 118 of system 100. The target device may verify that the anatomical feature is oriented toward the target via a verification image (captured by a camera other than camera system 106 such as, for example, a camera mounted on or affixed to the cell phone, another camera in the environment, etc.). In some embodiments, the cell phone may analyze the verification image utilizing any of a plurality of facial recognition methods, such as blob analysis, deep learning, Viola-Jones algorithm (inventors, verify and/or expand?), to determine if the face of the subject is oriented towards the cell phone. In the same or other embodiments, the cell phone may transmit the results of the image analysis as verification to system 100. In the same or other embodiments, the cell phone may transmit the verification image itself to system 100 for analysis by logic 122. Logic 122 may be configured to perform similar facial recognition analysis on the verification image.

In some embodiments, logic 122 may be configured to cause sound generation circuitry 114 to emit a directional sound, such that the directional sound appears to the anatomical feature as if emitted from a known target location. The emitted directional sound may advantageously cause subject 202 to turn to face the known target location. This may be particularly beneficial for several reasons. It may reduce or eliminate error resulting from subject 202 looking at a target without fully turning their head 204 to face the target (e.g., some systems may assume subject 202 is directly facing a stimulus when the user is actually "glancing sideways" at the stimulus, possibly introducing error into orientation determinations). As subjects (e.g., humans) may reflexively turn to face the source of a sound (particularly if the sound is unknown or unexpected), the possibility of subject 202 glancing without turning his/her head 204 toward the stimulus may be substantially reduced or eliminated. Further, the emitted directional sound may advantageously result in subject 202 turning to face a desired known location with minimal or no prior notification, prompting, or explanation of the task to the user. In other words, logic 122 may not need to educate, prompt, or instruct subject 202 on what to do, for how long, why, etc.; the subject may instead simply perform the desired task, advantageously simplifying system 100. In some embodiments, sound generation circuitry 114 may be configured to emit a directional sound of a particularly startling, surprising, or confusing nature (e.g., a buzzer, a prerecorded phrase, etc.) to decrease the probability of subject 202 ignoring or failing to notice the directional sound and to increase the probability of subject 202 turning his or her head 204 to directly face the desired location. However, in some embodiments, logic 122 may nonetheless provide instructions, prompts, warnings etc. to subject 202 prior to emitting the directional sound.

If the acoustic properties of the environment have changed (by, for example, the addition, relocation, modification, and/or removal of objects such as sofas, televisions, tables, walls, etc.), then the directional sound emitted by sound generation circuitry 114 may appear to subject 202 to be coming from a location other than the known location, which may introduce error into an anatomical feature orientation determination. Thus, in some embodiments, the acoustics of the directional sound may be compared to an expected value. For example, as described above, logic 120 may use sound generation circuitry 114 and microphone system 112 to determine acoustic properties of the environment. Microphone system 112 may also record the directional sound emitted by sound generation circuitry 114. The recorded directional sound may be stored in a storage device 110 or memory 104 and may be analyzed by logic 120 using, for example, Fourier Analysis on the frequency response, correlation analysis of the signals, etc. A predicted waveform may be determined by the logic 120 based upon the determined acoustic properties of the environment and the waveform of the directional sound emitted by the sound generation circuitry 114. Properties of the waveform of the recorded directional sound and the predicted waveform may be determined by logic 120. These properties may include, for example, time domain properties (frequency, amplitude, peak to peak time, etc.) or frequency domain properties (component frequencies, magnitudes/phases of the component frequencies, etc.). Logic 120 may compare these properties to verify, validate, or otherwise determine if the acoustic properties of the environment stored in storage device 110 or memory 104 are accurate. The comparison may be made using a threshold (e.g., 5% error, 1% error, etc.)

In some embodiments, orientation reference logic 122 may be configured to prompt subject 202 to emit sound (e.g., speak) in addition to orienting the head toward the target. In embodiments where the identified anatomical feature is not expected to emit sound (e.g., a camera), this may merely introduce error and thus may not be performed. However, in the same embodiments, logic 120 may be configured to utilize the subject-emitted sound to determine a general area of the subject, enabling logic 120 to rule out regions to analyze when determining a more specific location of anatomical feature 204 as described above. This may decrease the time or power required for anatomical feature location.

In some embodiments, logic 122 may use one or more sensors on the anatomical feature to determine its orientation. For example, logic 122 may communicate with (via, e.g., Bluetooth, WiFi, etc.) a compass and/or accelerometers and/or gyroscopes to measure orientation of the anatomical feature within an XYZ coordinate system. These sensors may provide information with, for example, 3 degrees of freedom (e.g., 3 1-dimensional accelerometers), 9 degrees of freedom (e.g., 3 gyroscopes, a 3-dimensional compass, and 3 1-dimensional accelerometers), etc. Location may be determined or tracked by logic 120 as described above, while orientation is determined by logic 122 using, e.g., dead reckoning, Kalman filtering, etc.

Figure 2:
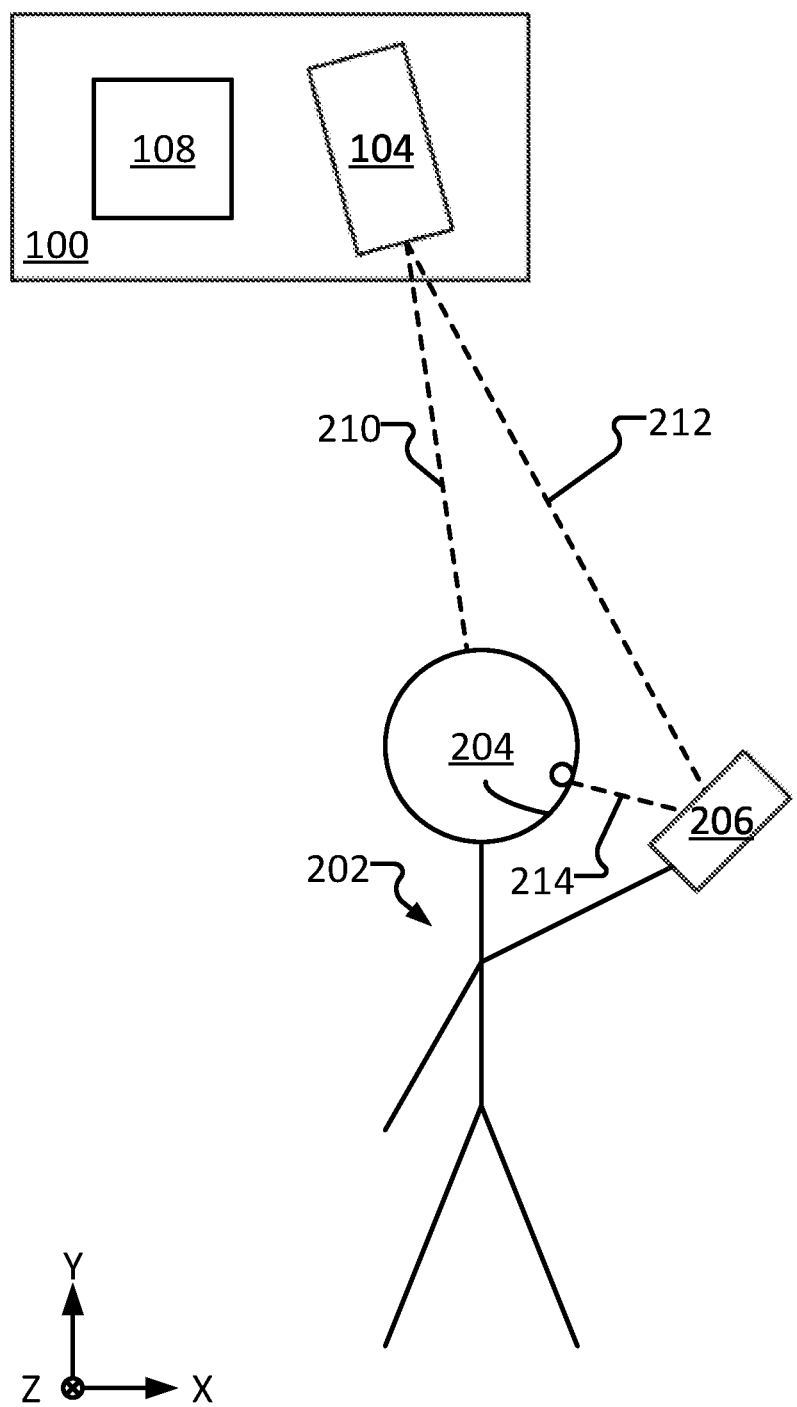
FIG. 2 illustrates an example environment in which the system is to operate.

These concepts are more clearly depicted in FIG. 2. FIG. 2 illustrates an example environment 200 in which the system 100 is to operate. In this example, certain elements of system 100 have been omitted for clarity. In this example, the environment 200 may be a closed room, open room, outdoor area, etc. In this example, a subject 202 is depicted within the field of view of camera system 106. The head of the subject 204 is generally oriented toward the object 206 in the subject's hand. As described above, logic 108 is configured to determine the location of the subject's head 204, in this example relative to a 3-space coordinate system (XYZ), and determine the first vector 210 representing the location of the subject's head and the distance of the subject's head from the camera system 106. Also, as described above, logic 108 is configured to determine the location of the object 206 as the identified target. In addition, logic 108 is configured to determine the second vector 212 representing the distance to the target object 206 from the camera system 106. To determine an orientation of the subject's head 204, logic 108 is also configured to determine the third vector 214 representing a direction of the subject's face toward the target object 206. In this example, the third vector 214 may be determined using vector sum analysis of vectors 210 and 212 (which may include 3 space vector matrices). For example, in an XYZ coordinate system, assuming the location of target 206 at x1, y1, and z1 and anatomical feature 204's location at x2, y2, z2, the vector of the anatomical feature orientation 214 may be determined as $(x2-x1)i+(y2-y1)j+(z2-z1)k$. The normalized direction of this vector may be determined by dividing the vector by its magnitude.

As described above, to cause the subject to look toward the target 206, logic 108 may also be configured to prompt the subject to point their head at target 206 (using, for example, audio prompts, video prompts, or, in some embodiments, by communicating with the target object 206 and providing instructions on the target object 206). In addition, logic 108 is configured to cause an image capture when the subject's head 204 is looking toward target object 206 and append metadata of the third vector 214 to the image.

While the foregoing description of FIGS. 1 and 2 are described with reference to using video image data to determine locations of the subject's head and the target object, in some embodiments, sound may be used to determine locations of the anatomical feature and target object, as described in relation to FIG. 5, below.

Figure 3:
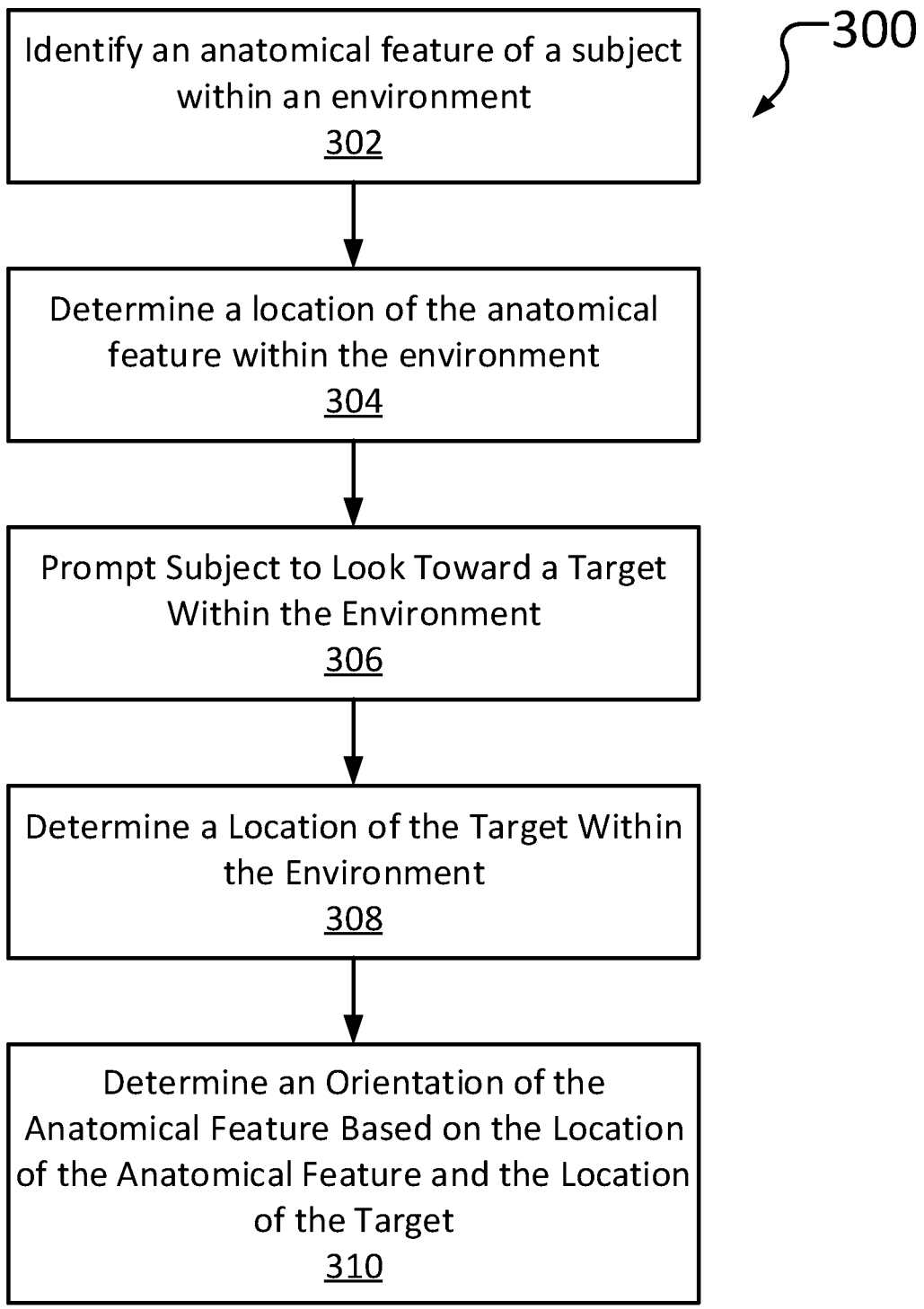
FIG. 3 illustrates operations according to one embodiment of the present disclosure.

FIG. 3 illustrates operations 300 according to one embodiment of the present disclosure. Operations according to this embodiment include identifying an anatomical feature of a subject within an environment 302. Operations further include determining a location of the anatomical feature within the environment 304. This may include, for example, determining a first vector representing a distance to the anatomical feature. Operations also include prompting the subject to look toward a target within the environment 306. Operations may also include determining a location of the target within the environment 308. This may include, for example, determining a second vector representing a distance to the target. Operations also include determining an orientation of the anatomical feature based on the location of the anatomical feature and the location of the target 310. This may include, for example, determining a third vector representing the direction the anatomical feature is oriented towards.

Figure 4:
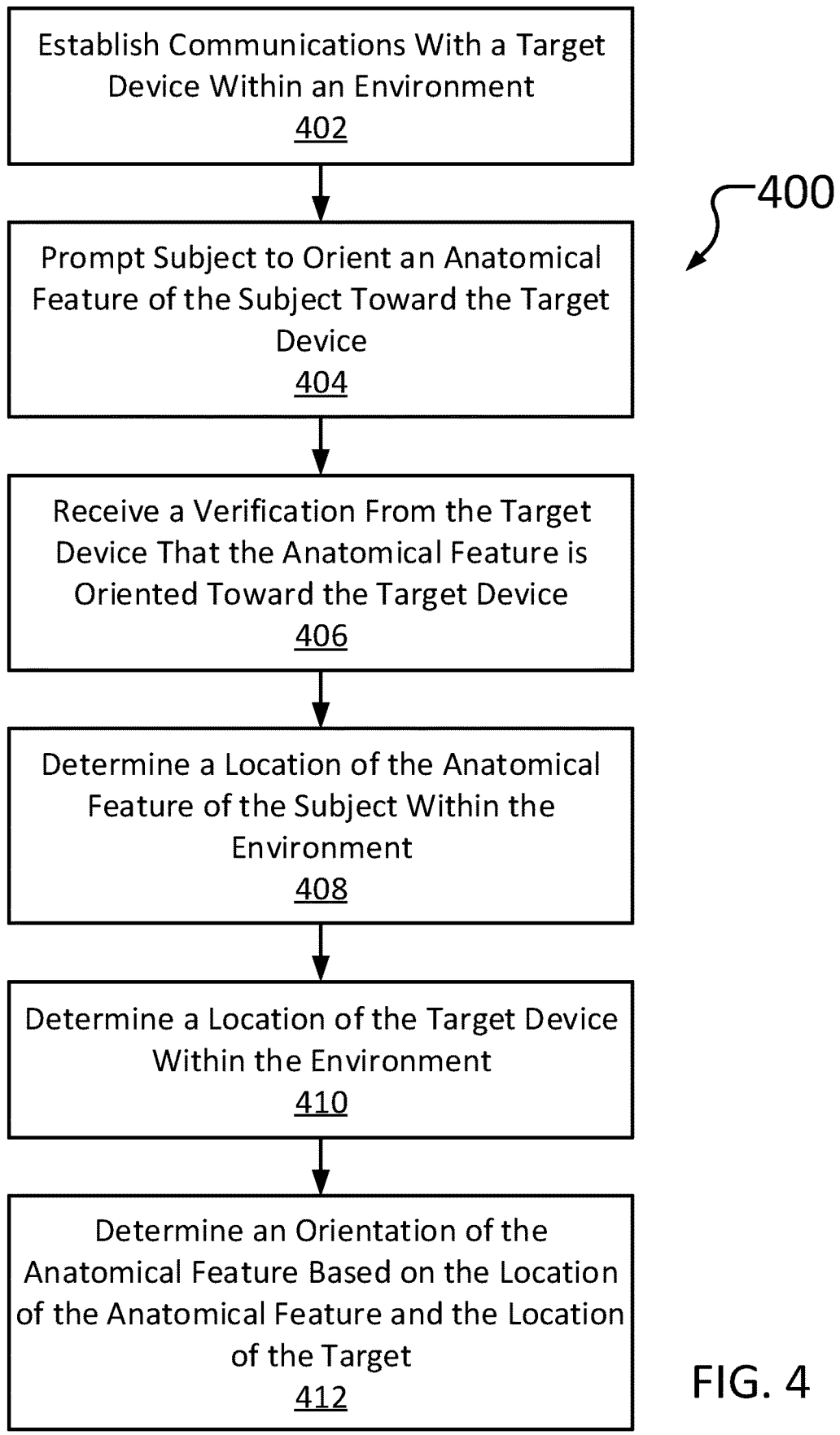
FIG. 4 illustrates operations according to one embodiment of the present disclosure.

FIG. 4 illustrates operations 400 according to one embodiment of the present disclosure. Operations according to this embodiment include establishing communications with a target device within an environment 402. This may include, for example, establishing a wired (e.g., Ethernet) or wireless (e.g., WiFi, Bluetooth, etc.) connection with the target device using communications circuitry 118. Operations further include prompting a subject to orient an anatomical feature of the subject toward the target device 404. Operations may also include receiving a verification (e.g., from the target device) that the anatomical feature of the subject is oriented toward the target device. This verification may include, for example, an image of the anatomical feature of the subject captured by a camera of the target device, a signal indicating that the anatomical feature of the subject is oriented toward the target device, etc. Operations further include determining a location of the anatomical feature of the subject within the environment 408. This may include, for example, determining a first vector representing a distance to the anatomical feature. Operations may also include determining a location of the target device within the environment 410. This may include, for example, determining a second vector representing a location to the target device. Operations also include determining an orientation of the anatomical feature based on the location of the anatomical feature and the location of the target device 412. This may include, for example, determining a third vector representing the direction the anatomical feature is oriented towards.

Figure 5:
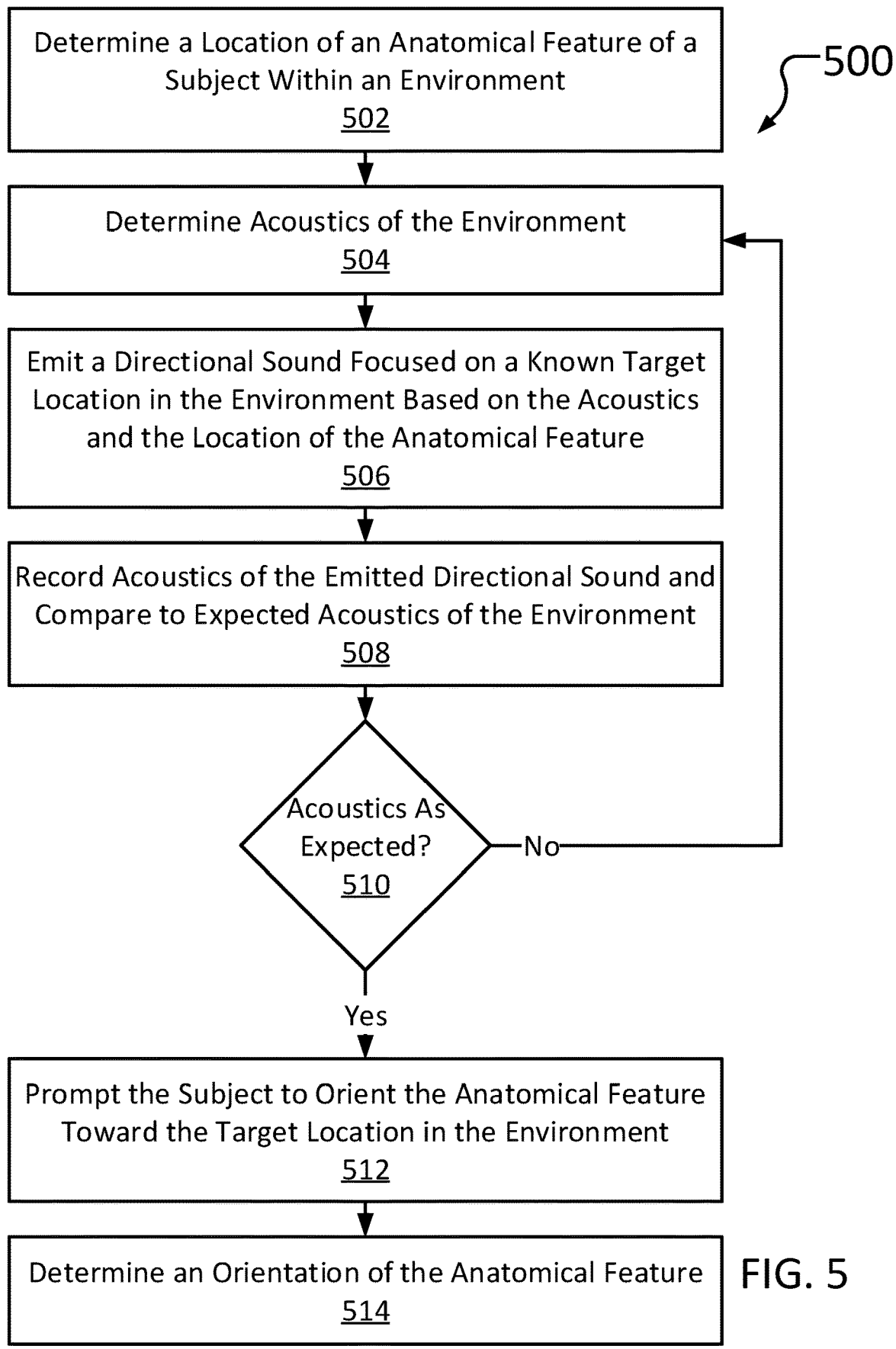
FIG. 5 illustrates operations according to one embodiment of the present disclosure.

FIG. 5 illustrates operations 500 according to one embodiment of the present disclosure. Operations according to this embodiment include determining a location of an anatomical feature of a subject within an environment 502. This may include, for example, determining a first vector representing a distance to the anatomical feature. Operations may also include determining acoustics of the environment 504. This may include, for example, emitting a sound into the environment using a speaker system, recording a resulting sound using a microphone system, and determining differences between the emitted and recorded sound (e.g., distortions, added noise, etc.). Operations also include emitting a directional sound focused on a known target location in the environment based on the acoustics and the location of the anatomical feature 506. This may include, for example, determining a directional sound waveform based on the location of the anatomical feature and the acoustics of the environment such that, when the determined directional sound waveform is emitted via a speaker system, when received at the location of the anatomical feature it appears as if emitted from the target location.

Operations of this embodiment may further include recording acoustics of the emitted directional sound and comparing them to expected acoustics of the environment 508. This may include, for example, determining an expected recorded waveform of the directional sound based on the determined acoustics of the environment and the waveform of the emitted directional sound, and comparing the expected waveform to the sound recorded by a microphone system. The comparison may be made using a threshold. If the acoustics of the recorded sound are outside the threshold of the expected waveform (510 "No"), operations may include re-determining the acoustics of the environment at 504. If the acoustics of the recorded sound are within the threshold (510 "Yes"), operations may further include prompting the subject to orient the anatomical feature toward the target location within the environment 512. Operations also include determining an orientation of the anatomical feature 514. This may include operations similar to 310 of FIG. 3 or 412 of FIG. 4, e.g., determining a second vector representing the distance to the known target location and determining a third vector representing the anatomical feature is oriented towards.

As described above, the determined direction 214 of the anatomical feature 204 may be assigned or appended to the captured image as metadata. The image combined with metadata may then be used as a reference or training input to a determination application. For example, the determination application may be configured to determine a pose of a head of a user without knowing a target location. The determination application may be configured as a machine learning system utilizing any of a plurality of machine learning methods such as, for example, regression algorithms, deep learning (including, for example, a convolutional neural networks (CNN), a recursive neural network (RNN), etc.). As these machine learning methods typically require "training" via sample images with known outcomes, the images and metadata from system 100 may be utilized as training inputs, enabling the application to compare its own predictions of feature orientation to the known values determined by system 100 as described above.

Reference is made throughout the present disclosure to an anatomical feature of a subject, e.g., a head of a human. However, this is meant merely as a non-limiting example; in some embodiments the subject may be any living entity, such as a dog, cat, fish, etc. In other embodiments, the subject may by a non-living entity, such as a robot, an unmanned aerial system/vehicle (UAS/UAV, including what is sometimes referred to as a "drone"), etc. Further, in some embodiments the anatomical feature may be any "component" of the subject, for example, a hand, a leg, etc. In some embodiments, the anatomical feature may be a component of an inanimate subject, for example a sensor pod of a robot. In other embodiments, the anatomical feature may be an object held by or connected to the subject, e.g., a camera, a phone, a wing, etc.

In some embodiments, system 100 may be configured to maintain and/or categorize data associated with a plurality of different subjects. For example, system 100 may determine several reference orientations of a first subject and capture images associated with those orientations. The resulting image-orientation data may be associated with the first subject. In the same or other embodiments, system 100 may additionally be configured to determine one or more reference orientations of an anatomical feature of a second subject, along with associated captured images, as described above. This may enable system 100 to train a machine learning application to better determine orientation of anatomical features of multiple subjects. Typical algorithms for object/face recognition may be applied to distinguish between subjects. Profiles of subjects may be stored, e.g., in a list or database on storage device 110, memory 104, etc. Anatomical feature location determination logic 120 may be configured to maintain the database, identifying if detected anatomical features are already listed in the database, and if they are, logic 120 may be further configured to associate further determinations with the entry in the database. Logic 122 may similarly associate determined orientation of the anatomical feature with its corresponding entry in the database. If no entry exists corresponding to the identified anatomical feature, system 100 may provide a prompt (via, e.g., user interface 116, sound generation circuitry 114, etc.) asking if a user wishes to create an entry, or if the identified feature belongs to an existing entry (e.g., if logic 120 was unable to determine if the identified anatomical feature is on the database already).

In some embodiments, system 100 may be configured to track and/or determine orientations and locations of the anatomical feature over time. For example, the anatomical feature may be in motion. In embodiments wherein logic 122 assumes that the anatomical feature 204 is directly oriented toward the stimulus, detection of motion of the anatomical feature may indicate that the subject is not responding or paying attention to the prompt, which may introduce error into the determination (e.g., if the anatomical feature is not actually oriented towards the target). However, in some embodiments, if the target is not stationary (e.g., if the target is a moving projected light, a robot, etc.) or potentially difficult to locate (e.g., the target is an apparent source of a directional sound), motion of the anatomical feature may be to be expected, so logic 120 may track motion (e.g., determine and record a location every second, every 0.5 seconds, every 0.01 seconds, etc.) and compare an amount of detected motion to a threshold (e.g., whether the anatomical feature of the subject has moved more than 0.5 meters in one second, etc.). The threshold may vary depending upon the nature of the target, the subject (in multi-subject embodiments, some subjects may be trusted to comply with prompts even if moving, etc.), error tolerance of the application to be trained, etc. In some embodiments, when prompting the subject to orient the anatomical feature towards the target, logic 122 may additional provide additional prompts or instructions that can be validated to verify that the subject is paying attention and/or complying with prompts.

In some embodiments, the target 206 may be controlled by system 100. For example, target 206 may be a robot or other mobile device that is capable of motion, or may be an image projected (via, e.g., image generation circuitry 124). In these or other embodiments, system 100 may cause target 206 to move before, during or after prompting subject 202 to orient anatomical feature 204 towards target 206. This may enable system 100 to make multiple determinations of anatomical feature orientation (as described above) in varied orientation scenarios. For example, if target 206 is a robot moving around in environment 200, images captured by camera system 106 may depicted subject 202 looking toward target 206 in multiple different orientations. These images (and their associated orientation metadata), if used as training inputs to a machine learning application as described above, may result in a more diversely-trained application; while multiple images of the same (or similar) orientations, target locations, etc. may still be useful, supervised machine learning applications benefit from (and may require) diverse training sets, especially those using personalized models as described above.

With continued reference to FIGS. 1 and 2, processor 102 may comprise one or more processors situated in separate components, or alternatively, one or more processing cores embodied in a single component (e.g., in a System-on-a-Chip (SoC) configuration) and any processor-related support circuitry (e.g., bridging interfaces, etc.). Example processors may include, but are not limited to, various x86-based microprocessors available from the Intel Corporation including those in the Pentium, Xeon, Itanium, Celeron, Atom, Quark, Core i-series, Core M-series product families, Advanced RISC (e.g., Reduced Instruction Set Computing) Machine or "ARM" processors, etc. Examples of support circuitry may include chipsets (e.g., Northbridge, Southbridge, etc. available from the Intel Corporation) configured to provide an interface through which processor 102 may interact with other system components that may be operating at different speeds, on different buses, etc. in system 100. Some or all of the functionality commonly associated with the support circuitry may also be included in the same physical package as the processor (e.g., such as in the Sandy Bridge family of processors available from the Intel Corporation).

Information (e.g., instructions, data, etc.) may be stored in memory 104. Memory 104 may comprise random access memory (RAM) and/or read-only memory (ROM) in a fixed or removable format. RAM may include volatile memory configured to hold information during the operation of system 100 such as, for example, static RAM (SRAM) or Dynamic RAM (DRAM). ROM may include nonvolatile (NV) memory modules configured based on BIOS, UEFI, etc. to provide instructions when system 100 is activated, programmable memories such as electronic programmable ROMs (EPROMS), Flash, etc. Other fixed/removable memory may include, but are not limited to, magnetic memories such as, for example, floppy disks, hard drives, etc., electronic memories such as solid state flash memory (e.g., embedded multimedia card (eMMC), etc.), removable memory cards or sticks (e.g., micro storage device (uSD), USB, etc.), optical memories such as compact disc-based ROM (CD-ROM), Digital Video Disks (DVD), Blu-Ray Disks, etc.

Camera system 106 may be controlled by processor 102 to record images or videos, which may be stored in storage device 110, memory 104, onboard memory of camera system 106 (not shown), etc. Camera system 106 may be any of a plurality of types of camera, including, for example, a typical red-green-blue (RGB) camera, a depth camera (e.g., a Time of Flight (TOF) camera), an infrared camera (e.g., a forward looking infrared (FLIR) camera), etc. The image(s) recorded by camera system 106 may vary depending upon the type of camera system 106; i.e., RGB camera images may be in color or black and white, while FLIR camera images may be white-hot or black-hot, etc. The various properties of image(s) recorded by camera system 106 (resolution, color depth, compression, file size, file type, etc.) may vary depending upon specifications of camera system 106 or on system 100. As a non-limiting example, in one embodiment camera system 106 may be a customer-off-the-shelf (CotS) RGB camera which may by default record JPEG images with a resolution of 1920×1080 pixels with 32-bit color depth using JPEG compression algorithms, but processor 102 may reconfigure camera system 106 to record uncompressed bitmap images with 16-bit color depth instead. In the same or other embodiments, processor 102 may convert images recorded by camera system 106 and stored in memory 104 from one type to another (e.g., from Portable Network Graphics (png) to Tagged Image File Format (tiff)). In the same or other embodiments, processor 102 may modify images from camera system 106 in other ways, such as, for example, stretching, rotating, translating, cropping, etc. These conversions may depend upon the configuration of a machine learning user head pose determination system (not shown), or upon the configuration or limitations of components or aspects of system 100 (e.g., memory 104, an operating system (OS), etc.).

Camera system 106 may be located in any of a plurality of locations in environment 200, such as, for example, the ceiling, a wall, the floor, etc. Camera system 106 may be mounted, attached, fixed, or otherwise coupled in place to a surface of environment 200. In some embodiments, camera system 106 may be movably attached to a surface (e.g., a track). In the same or other embodiments, camera system 106 may be coupled to a housing of system 100. In some embodiments, camera system 106 may be resting in place (i.e., not be attached or fixed to any surface).

Camera system 106 may have any of a plurality of optical configurations, including, for example, an ultra-wide angle lens (such as a fisheye lens), a zoom lens, a macro lens, etc. In some embodiments, camera system 106 may be implemented as a pair of cameras utilizing a pair of stereoscopic lenses to produce pairs of images. Processor 102 may be configured to perform "de-warping" operations upon images captured by camera system 106 to account for any optical distortion caused by the lens, etc. The de-warping operations may depend upon the configuration or needs of a machine learning application.

The location or position of camera system 106 may be known relative to a coordinate system (e.g., XYZ). The coordinate system may be centered about any of a plurality of positions or objects including, for example, camera system 106 (i.e., camera is at the origin), subject 202, target 206, a landmark in environment 200 (e.g., a chair, a painting, etc.), a component of system 100 (e.g., a center of the housing of system 100, in embodiments wherein system 100 has a housing), or a geological coordinate (e.g., a corner of room 100, a center of room 100, a latitude/longitude/elevation coordinate, the center of the Earth, etc.). The location of camera system 106 may be stored relative to the coordinate system in memory 104, in a cache (not shown in FIG. 1) of processor 102, in an onboard memory of camera system 106 (not shown in FIG. 1), in a memory of a remote server, etc. In some embodiments, system 100 may assume camera system 106's position to be a predetermined value relative to the coordinate system. In the same or other embodiments, system 100 may be configured to determine the position of camera system 106 via image analysis, as will be described in further detail below. In the same or other embodiments, camera system 106's position may be input to system 100, e.g. by subject 202 via user interface 116 or target 206.

In embodiments wherein camera system 106 is mobile (e.g., on a track, unattached to any surface, etc.), system 100 may include one or more sensors to determine or update the position of camera system 106. For example, camera system 106 may have one or more accelerometers mounted, attached, or otherwise coupled to it. Thus, when camera system 106 moves, the data from the accelerometer(s) can be used to determine how far camera system 106 has moved from its previous position, and in which direction. In some embodiments, the track may utilize optical sensors to determine the position of the camera on the track.

Sound generation circuitry 114 may include, for example, one or more speakers, sirens, dynamic microphones, etc. As described above, sound generation circuitry 114 may be utilized or controlled by anatomical orientation determination logic 108 to provide notifications or directions to subject 202. For example, sound generation circuitry 114 may direct subject 202 to look at target 206 for a period of time (e.g., playing a prerecorded or dynamically synthesized voice saying "please look at your phone for 3 seconds," 5 seconds, 20 seconds, etc.) to enable logic 108 to determine an accurate orientation of an anatomical feature. Sound generation circuitry 114 may also notify subject 202 when subject 202 may stop looking at the target, e.g., if determination of feature orientation (and associated image capture) is complete, or if determination is unsuccessful.

In some embodiments, subject 202 may need to directly face target 206 for a predetermined amount of time. In the same or other embodiments, orientation reference logic 122 may specify a duration of time and/or instruct subject 202 to face target 206 directly. System 100 may prompt subject 202 in any of a plurality of ways, such as, for example, providing a notification via user interface 116 (e.g., via a display, haptic feedback, etc.) or sound generation circuitry 114 (e.g., via a chime or audible instruction). In some embodiments, target 206 may be a device capable of communication with system 100 (e.g., a computer, mobile phone, fob, television, robot, etc.). In the same or other embodiments, system 100 may communicate with target device 206 (via communications circuitry 118 using wired or wireless communication, such as WiFi, Bluetooth, near-field communications (NFC), radio frequency (RF) communications, etc.) to have target 206 prompt subject 202 to perform an action, such as to orient anatomical feature 204 toward target 206. In some embodiments, orientation reference logic 122 may instruct target 206 to display text for subject 202 to read. Logic 122 may also prompt subject 202 to remain stationary while looking at target 206. In some embodiments, system 100 may communicate with target 206 to verify that subject 202 is looking directly at target 206. For example, in embodiments where target 206 is a smartphone with a camera (e.g., Samsung Galaxy S8, IPhone 6, etc.), logic 122 may transmit a signal to cause target 206 to capture an image of anatomical feature 204 and transmit the image to system 100 (via communication methods as described above; WiFi, Bluetooth, etc.).

Operations for the embodiments have been described with reference to the above figures and accompanying examples. Some of the figures may include a logic flow. Although such figures presented herein may include a particular logic flow, it can be appreciated that the logic flow merely provides an example of how the general functionality described herein can be implemented. Further, the given logic flow does not necessarily have to be executed in the order presented unless otherwise indicated. In addition, the given logic flow may be implemented by a hardware element, a software element executed by a processor, or any combination thereof. The embodiments are not limited to this context.

Various features, aspects, and embodiments have been described herein. The features, aspects, and embodiments are susceptible to combination with one another as well as to variation and modification, as will be understood by those having skill in the art. The present disclosure should, therefore, be considered to encompass such combinations, variations, and modifications. Thus, the breadth and scope of the present invention should not be limited by any of the above-described exemplary embodiments, but should be defined only in accordance with the following claims and their equivalents.

The terms and expressions which have been employed herein are used as terms of description and not of limitation, and there is no intention, in the use of such terms and expressions, of excluding any equivalents of the features shown and described (or portions thereof), and it is recognized that various modifications are possible within the scope of the claims. Accordingly, the claims are intended to cover all such equivalents. Various features, aspects, and embodiments have been described herein. The features, aspects, and embodiments are susceptible to combination with one another as well as to variation and modification, as will be understood by those having skill in the art. The present disclosure should, therefore, be considered to encompass such combinations, variations, and modifications.

Reference throughout this specification to "one embodiment" or "an embodiment" means that a particular feature, structure, or characteristic described in connection with the embodiment is included in at least one embodiment. Thus, appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

As used in any embodiment herein, the term "logic" may refer to software, firmware and/or circuitry configured to perform any of the aforementioned operations. Software may be embodied as a software package, code, instructions, instruction sets and/or data recorded on non-transitory computer readable storage mediums. Firmware may be embodied as code, instructions or instruction sets and/or data that are hard-coded (e.g., nonvolatile) in memory devices. "Circuitry", as used in any embodiment herein, may comprise, for example, singly or in any combination, hardwired circuitry, programmable circuitry such as computer processors comprising one or more individual instruction processing cores, state machine circuitry, and/or firmware that stores instructions executed by programmable circuitry. The logic may, collectively or individually, be embodied as circuitry that forms part of a larger system, for example, an integrated circuit (IC), system on-chip (SoC), desktop computers, laptop computers, tablet computers, servers, smartphones, etc.

The following examples pertain to further embodiments. The following examples of the present disclosure may comprise subject material such as an apparatus, a method, at least one machine-readable medium for storing instructions that when executed cause a machine to perform acts based on the method, means for performing acts based on the method and/or a system for anatomical feature orientation determination.

According to example 1, there is provided an apparatus capable of determining an orientation of an anatomical feature. The apparatus may comprise anatomical feature location determination logic to identify an anatomical feature of a subject within an environment and determine a location of the anatomical feature of the subject within the environment, and orientation reference logic to prompt the subject to orient the anatomical feature toward a target within the environment, determine a location of the target within the environment, and determine an orientation of the anatomical feature based on the location of the anatomical feature and the location of the target.

Example 2 may include the elements of example 1, wherein the orientation reference logic is further to cause a camera to capture an image of the anatomical feature of the subject oriented toward the location of the target.

Example 3 may include the elements of example 2, wherein the orientation reference logic is further to determine metadata based upon the determined orientation of the anatomical feature and associate the metadata with the captured image.

Example 4 may include the elements of any of examples 1 to 3, wherein the orientation reference logic is to prompt the subject to orient the anatomical feature toward the target within the environment by causing sound generation circuitry to emit a sound or causing image generation circuitry to emit a visual cue.

Example 5 may include the elements of any of examples 1 to 4, wherein orientation reference logic is further to cause communications circuitry to establish a communications link with the target, cause the communications circuitry to transmit an instruction to the target, and cause the communications circuitry to receive a verification signal from the target, wherein the verification signal is to indicate that the anatomical feature is oriented toward the target.

Example 6 may include the elements of any of examples 1 to 5, wherein the anatomical feature is a head of the subject.

Example 7 may include the elements of any of examples 1 to 6, wherein the anatomical feature location determination logic is further to maintain a list of known anatomical features of known subjects.

Example 8 may include the elements of example 7, wherein the anatomical feature location determination logic to identify an anatomical feature of a subject within an environment comprises anatomical feature location determination logic to identify an anatomical feature of a subject selected from the list of known anatomical features of known subjects.

Example 9 may include the elements of any of examples 7 or 8, wherein the orientation reference logic is further to associate the determined orientation of the anatomical feature with a known anatomical feature selected from the list.

Example 10 may include the elements of any of examples 1 to 9, wherein the anatomical feature location determination logic is further to determine whether the anatomical feature is in motion.

Example 11 may include the elements of any of examples 1 to 10, wherein anatomical feature location determination logic is further to track locations of the anatomical feature over time.

Example 12 may include the elements of any of claims 1 to 3, wherein the target is a target location in the environment, the anatomical feature location determination logic is further to cause sound generation circuitry to emit a sound into the environment, cause a microphone system to record at least the emitted sound, compare the emitted sound to the recorded sound, determine acoustic properties of the environment based, at least in part, on the comparison, and determine a directional sound waveform based, at least in part, on the determined acoustic properties of the environment, and wherein the anatomical feature location determination logic to prompt the subject to orient the anatomical feature toward a target within the environment comprises anatomical feature location determination logic to cause the sound generation circuitry to emit a directional sound into the environment based on the determined directional sound waveform, wherein the emitted directional sound is to be heard at the determined location of the anatomical feature as if emitted from the target location.

According to example 13 there is provided a system for determining an orientation of an anatomical feature. The system may comprise a storage device to store at least images and data, anatomical feature location determination logic to identify an anatomical feature of a subject within an environment and determine a location of the anatomical feature of the subject within the environment, and orientation reference logic to prompt the subject to orient the anatomical feature toward a target within the environment, determine a location of the target within the environment, and determine an orientation of the anatomical feature based on the location of the anatomical feature and the location of the target.

Example 14 may include the elements of example 13, wherein the orientation reference logic is further to cause a camera to capture an image of the anatomical feature of the subject oriented toward the location of the target and store the captured image on the storage device.

Example 15 may include the elements of example 14, wherein the orientation reference logic is further to determine metadata based, at least in part, on the determined orientation and associate the metadata with the captured image.

Example 16 may include the elements of any of examples 13 to 15, and may further comprise sound generation circuitry and image generation circuitry, wherein the orientation reference logic is to prompt the subject to orient the anatomical feature toward the target within the environment by causing the sound generation circuitry to emit a sound or causing the image generation circuitry to emit a visual cue.

Example 17 may include the elements of any of examples 13 to 16, and may further comprise communications circuitry, wherein the orientation reference logic is further to cause the communications circuitry to establish a communications link with the target, transmit an instruction to the target, and receive a verification signal from the target, the verification signal to indicate that the anatomical feature is oriented toward the target.

Example 18 may include the elements of any of examples 13 to 17, wherein the anatomical feature is a head of the subject.

Example 19 may include the elements of any of examples 13 to 18, wherein the anatomical feature location determination logic is further to maintain a list of known anatomical features of known subjects.

Example 20 may include the elements of example 19, wherein the anatomical feature location determination logic to identify an anatomical feature of a subject within an environment may comprise anatomical feature location determination logic to identify an anatomical feature of a subject selected from the list of known anatomical features of known subjects.

Example 21 may include the elements of any of examples 19 or 20, wherein the orientation reference logic is further to associate the determined orientation of the anatomical feature with a known anatomical feature selected from the list.

Example 22 may include the elements of any of examples 13 to 21, wherein the anatomical feature location determination logic is further to determine whether the anatomical feature is in motion.

Example 23 may include the elements of any of examples 13 to 22, wherein anatomical feature location determination logic is further to track locations of the anatomical feature over time.

Example 24 may include the elements of any of examples 13 to 15, and may further comprise sound generation circuitry and a microphone system, wherein the target is a target location in the environment, the anatomical feature location determination logic is further to cause the sound generation circuitry to emit a sound into the environment, cause the microphone system to record at least the emitted sound, compare the emitted sound to the recorded sound, determine acoustic properties of the environment based, at least in part, on the comparison, and determine a directional sound waveform based, at least in part, on the determined acoustic properties of the environment, and wherein the anatomical feature location determination logic to prompt the subject to orient the anatomical feature toward a target within the environment comprises anatomical feature location determination logic to cause the sound generation circuitry to emit a directional sound into the environment based on the determined directional sound waveform, wherein the emitted directional sound is to be heard at the determined location of the anatomical feature as if emitted from the target location.

According to example 25 there is provided a method for determining an orientation of an anatomical feature. The method may comprise identifying, via anatomical feature location determination logic, an anatomical feature of a subject within an environment, determining, via the anatomical feature location determination logic, a location of the anatomical feature of the subject within the environment, prompting, via orientation reference logic, the subject to orient the anatomical feature toward a target within the environment, determining, via the orientation reference logic, a location of the target within the environment, and determining, via the orientation reference logic, an orientation of the anatomical feature based on the location of the anatomical feature and the location of the target.

Example 26 may include the elements of example 25, and may further comprise causing, via the orientation reference logic, a camera to capture an image of the anatomical feature of the subject oriented toward the location of the target.

Example 27 may include the elements of example 26, and may further comprise generating, via the orientation reference logic, metadata based upon the determined orientation of the anatomical feature, associating the metadata with the captured image, and storing, on a storage device, the captured image and associated metadata.

Example 28 may include the elements of any of examples 25 to 27, wherein prompting, via orientation reference logic, the subject to orient the anatomical feature toward a target within the environment may comprise emitting, via sound generation circuitry, a sound to prompt the subject to orient the anatomical feature toward a target within the environment, or emitting, via image generation circuitry, a visual cue to prompt the subject to orient the anatomical feature toward a target within the environment.

Example 29 may include the elements of any of examples 25 to 28, and may further comprise establishing, via communications circuitry, a communications link with the target, transmitting, via the communications circuitry, an instruction to the target, and receiving, via the communications circuitry, a verification signal from the target, the verification signal to indicate that the anatomical feature is oriented toward the target.

Example 30 may include the elements of any of examples 25 to 29, wherein the anatomical feature is a head of the subject.

Example 31 may include the elements of any of examples 25 to 30, and may further comprise maintaining, via the anatomical feature location determination logic, a list of known anatomical features of known subjects.

Example 32 may include the elements of example 31, wherein identifying, via anatomical feature location determination logic, an anatomical feature of a subject within an environment comprises identifying, via anatomical feature location determination logic, an anatomical feature of a subject selected from the list of known anatomical features of known subjects.

Example 33 may include the elements of examples 31 or 32, and may further comprise associating, via the orientation reference logic, the determined orientation of the anatomical feature with a known anatomical feature selected from the list.

Example 34 may include the elements of any of examples 25 to 33, and may further comprise determining, via the anatomical feature location determination logic, whether the anatomical feature is in motion.

Example 35 may include the elements of any of examples 25 to 34, and may further comprise tracking, via the anatomical feature location determination logic, locations of the anatomical feature over time.

Example 36 may include the elements of any of examples 25 to 27, and may further comprise causing, via the anatomical feature location determination logic, sound generation circuitry to emit a sound into the environment, causing, via the anatomical feature location determination logic, a microphone system to recording, via the anatomical feature location determination logic, at least the emitted sound, comparing, via the anatomical feature location determination logic, the emitted sound to the recorded sound, determining, via the anatomical feature location determination logic, acoustic properties of the environment based, at least in part, on the comparison, determining, via the anatomical feature location determination logic, a directional sound waveform based, at least in part, on the determined acoustic properties of the environment, wherein the target is a target location in the environment, and prompting, via orientation reference logic, the subject to orient the anatomical feature toward a target within the environment comprises causing, via the orientation reference logic, the sound generation circuitry to emit a directional sound into the environment based on the determined directional sound waveform, wherein the emitted directional sound is to be heard at the determined location of the anatomical feature as if emitted from the target location.

According to example 37 there is provided a system including at least one device, the system being arranged to perform the method of any of the above examples 25 to 36.

According to example 38 there is provided a chipset arranged to perform the method of any of the above examples 25 to 36.

According to example 39 there is provided at least one machine readable storage device have a plurality of instructions stored thereon which, when executed on a computing device, cause the computing device to carry out the method according to any of the above examples 25 to 36.

According to example 40 there is provided at least one apparatus configured for anatomical feature orientation determination, the at least one device being arranged to perform the method of any of the above examples 25 to 36.

According to example 41 there is provided a system for determining an orientation of an anatomical feature. The system may comprise means for identifying an anatomical feature of a subject within an environment, means for determining a location of the anatomical feature of the subject within the environment, means for prompting the subject to orient the anatomical feature toward a target within the environment, means for determining a location of the target within the environment, and means for determining an orientation of the anatomical feature based on the location of the anatomical feature and the location of the target.

Example 42 may include the elements of example 41, and may further comprise means for causing a camera to capture an image of the anatomical feature of the subject oriented toward the location of the target, and means for storing the captured image on the storage device. Example 43 may include the elements of example 42, and may further comprise means for determining metadata based, at least in part, on the determined orientation, and means for associating the metadata with the captured image.

Example 44 may include the elements of any of examples 41 to 43 wherein the means for prompting the subject to orient the anatomical feature toward a target within the environment may comprise means for causing sound generation circuitry to emit a sound, or means for causing image generation circuitry to emit a visual cue.

Example 45 may include the elements of any of examples 41 to 44, and may further comprise means for causing communications circuitry to establish a communications link with the target, means for causing the communications circuitry to transmit an instruction to the target, and means for causing the communications circuitry to receive a verification signal from the target, the verification signal to indicate that the anatomical feature is oriented toward the target.

Example 46 may include the elements of any of examples 41-45, wherein the anatomical feature is a head of the subject.

Example 47 may include the elements of any of examples 41-46, and may further comprise means for maintaining a list of known anatomical features of known subjects.

Example 48 may include the elements of example 47, wherein the means for identifying an anatomical feature of a subject within an environment may comprise means for identifying an anatomical feature of a subject selected from the list of known anatomical features of known subjects.

Example 49 may include the elements of any of examples 47 or 48, and may further comprise means for associating the determined orientation of the anatomical feature with a known anatomical feature selected from the list.

Example 50 may include the elements of any of examples 41 to 49, and may further comprise means for determining whether the anatomical feature is in motion.

Example 51 may include the elements of any of examples 41 to 50, and may further comprise means for tracking locations of the anatomical feature over time.

Example 52 may include the elements of any of examples 41 to 43, and may further comprise means for causing sound generation circuitry to emit a sound into the environment, means for causing a microphone system to record at least the emitted sound, means for comparing the emitted sound to the recorded sound, means for determining acoustic properties of the environment based, at least in part, on the comparison, and means for determining a directional sound waveform based, at least in part, on the determined acoustic properties of the environment, wherein the means for prompting the subject to orient the anatomical feature toward a target within the environment may comprise means for causing the sound generation circuitry to emit a directional sound into the environment based on the determined directional sound waveform, wherein the emitted directional sound is to be heard at the determined location of the anatomical feature as if emitted from the target, wherein the target is a target location in the environment.

The terms and expressions which have been employed herein are used as terms of description and not of limitation, and there is no intention, in the use of such terms and expressions, of excluding any equivalents of the features shown and described (or portions thereof), and it is recognized that various modifications are possible within the scope of the claims. Accordingly, the claims are intended to cover all such equivalents.

What is claimed is:

1. An apparatus for determining an orientation of an anatomical feature of a subject, the apparatus comprising:
   memory;
   instructions;
   processor circuitry to execute the instructions to:
      identify an anatomical feature of the subject;
      determine a first location of the anatomical feature at a first time;
      determine a second location of the anatomical feature at a second time;
      determine a motion of the anatomical feature based on the first location and the second location; and
      determine the orientation of the anatomical feature of the subject based on a location of a target and the motion.

2. The apparatus of claim 1, wherein the processor circuitry is to provide a prompt to the subject to turn toward the target.

3. The apparatus of claim 2, wherein the processor circuitry is to:
   perform a comparison of the motion to a threshold; and
   determine a compliance of the subject to the prompt based on the comparison.

4. The apparatus of claim 3, wherein the threshold is based on the target.

5. The apparatus of claim 2, wherein the prompt is a sound.

6. The apparatus of claim 2, wherein the prompt is a movement of the target.

7. The apparatus of claim 2, wherein the prompt is an instruction to look at the target for a threshold amount of time.

8. The apparatus of claim 1, wherein the target is an object separate from a camera, the processor circuitry to determine the orientation based on a location of the camera.

9. The apparatus of claim 8, wherein the camera and the target are independently mobile.

10. A machine readable storage device comprising instructions, which when executed, cause programmable circuitry to at least:

determine a motion of an anatomical feature of a subject based on a change in a location of the anatomical feature over time;

determine a location of a target; and determine an orientation of the anatomical feature of the subject based on the motion and the location of the target.

11. The storage device of claim 10, wherein the instructions cause the programmable circuitry to give a command for the subject to take an action with respect to the target.

12. The storage device of claim 11, wherein the instructions cause the programmable circuitry to:

perform a comparison of the motion to a threshold; and determine a compliance of the subject to the command based on the comparison.

13. The storage device of claim 12, wherein the threshold is based on the target.

14. The storage device of claim 11, wherein the command is to look at the target for a threshold amount of time.

15. The storage device of claim 10, wherein the instructions cause the programmable circuitry to move the target to cause the subject to take an action with respect to the target.

16. The storage device of claim 10, wherein the target is an object separate from a camera, the instructions cause the programmable circuitry to determine the orientation based on a location of the camera.

17. A method of determining an orientation of a body part a subject, the method comprising:

accessing, by executing instructions with a processor, location data of a camera;

accessing, by executing instructions with the processor, location data of a target;

determining, by executing instructions with the processor, a motion of the body part based on a change in location of the body part; and determining, by executing instructions with the processor, the orientation of the body part based in the location data of the camera, the location data of the target, and the motion of the body part.

18. The method of claim 17, further including inducing the motion of the body part by causing the target to move.

19. The method of claim 17, further including:

providing instructions for the subject to take an action relative to the target;

performing a comparison of the motion to a threshold; and determining an observance of the instructions by the subject based on the comparison.

20. The method of claim 19, wherein the threshold is based on the subject.

* * * * *